United States Patent
Talgorn et al.

(10) Patent No.: US 11,234,660 B2
(45) Date of Patent: Feb. 1, 2022

(54) PATIENT POSITIONING IN DIAGNOSTIC IMAGING

(71) Applicant: KONINKLIJKE PHILIPS N.V., Eindhoven (NL)

(72) Inventors: Elise Claude Valentine Talgorn, Eindhoven (NL); Johan Partomo Djajadiningrat, Utrecht (NL); Sven Weichert, Waalre (NL); Thomas Rohse, Braak (DE); Rik August Runge, Tilburg (NL); Gyeol Han, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 35 days.

(21) Appl. No.: 16/954,581

(22) PCT Filed: Dec. 18, 2018

(86) PCT No.: PCT/EP2018/085527
§ 371 (c)(1),
(2) Date: Jun. 17, 2020

(87) PCT Pub. No.: WO2019/121702
PCT Pub. Date: Jun. 27, 2019

(65) Prior Publication Data
US 2020/0330055 A1    Oct. 22, 2020

(30) Foreign Application Priority Data
Dec. 18, 2017 (EP) .................................... 17208076

(51) Int. Cl.
*A61B 6/04* (2006.01)
*A61B 6/00* (2006.01)
(Continued)

(52) U.S. Cl.
CPC .............. *A61B 6/0487* (2020.08); *A61B 6/42* (2013.01); *A61B 6/461* (2013.01); *A61B 6/545* (2013.01);
(Continued)

(58) Field of Classification Search
CPC ......... A61B 6/0487; A61B 6/42; A61B 6/461; A61B 6/545; A61B 6/547; A61B 5/055;
(Continued)

(56) References Cited

U.S. PATENT DOCUMENTS 3,845,313 A   10/1974 Nosol
5,823,192 A   10/1998 Kalend
(Continued)

FOREIGN PATENT DOCUMENTS

DE    102006048607 A1    4/2008
WO    WO2016092797 A1    6/2016
WO    WO-2016092797 A1 *  6/2016 ........... A61B 5/0091

OTHER PUBLICATIONS

PCT International Search Report, International application No. PCT/EP2018/085527 dated Apr. 26, 2019.

*Primary Examiner* — Courtney D Thomas
(74) *Attorney, Agent, or Firm* — Larry Liberchuk

(57) ABSTRACT

A positioning system (10) for positioning a patient (101) for diagnostic imaging is provided. The system comprises a sensor arrangement (12) with at least one sensor (14, 16) configured to provide a sensor signal indicative of at least one body parameter of the patient (101), a controller (18) configured to determine a value of the at least one body parameter based on the sensor signal of the at least one sensor (14, 16), and at least one actuatable support (20) configured to move at least one of an arm (105) and a leg (107) of the patient with respect to a torso of the patient. Therein, the controller (18) is configured to actuate the at
(Continued)

least one actuatable support (20) depending on the determined value of the at least one body parameter to move at least one of the arm and the leg relative to the torso of the patient, such that the patient is guided to a posture for diagnostic imaging.

15 Claims, 7 Drawing Sheets

(51) Int. Cl.
*A61B 8/00* (2006.01)
*G01L 5/00* (2006.01)
*A61B 5/055* (2006.01)

(52) U.S. Cl.
CPC ............... *A61B 6/547* (2013.01); *G01L 5/00* (2013.01); *A61B 5/055* (2013.01); *A61B 8/40* (2013.01)

(58) Field of Classification Search
CPC .......... A61B 8/40; A61B 5/1114; A61B 6/08; A61B 6/563; A61B 6/04; A61B 5/702; G01L 5/00
See application file for complete search history.

(56) References Cited

U.S. PATENT DOCUMENTS

| | | |
|---|---|---|
| 2004/0122311 A1 | 6/2004 | Cosman |
| 2005/0228255 A1 | 10/2005 | Saracen |
| 2006/0288483 A1 | 12/2006 | Naslund |
| 2010/0228155 A1 | 9/2010 | Yang |
| 2011/0226959 A1 | 9/2011 | Boudier |
| 2016/0354037 A1 | 12/2016 | Breen |
| 2017/0035374 A1 | 2/2017 | Schafer |
| 2017/0322484 A1 | 11/2017 | Erhard |

* cited by examiner

PATIENT POSITIONING IN DIAGNOSTIC IMAGING

FIELD OF THE INVENTION

Generally, the invention concerns the field of diagnostic imaging, such as e.g. X-ray imaging. Particularly, the invention concerns a positioning system for positioning a patient for diagnostic imaging, an X-ray imaging apparatus comprising such positioning system, and a method for operating such positioning system.

BACKGROUND OF THE INVENTION

In diagnostic imaging, the number of patients that can be handled by a single diagnostic imaging apparatus per day, which may also be referred to as patient throughput, may have a direct effect on costs of hospitals. For this reason, the patient throughput may be taken into account in the design of diagnostic imaging apparatuses and/or any other healthcare equipment.

For example, in diagnostic X-Ray imaging (DXR) the total time required per patient to acquire an X-ray image may be a relevant consideration for the design of an X-ray imaging apparatus. Therein, the time required may not only be influenced by the speed of the X-ray imaging apparatus itself, e.g. how long it takes to move the X-ray tube in position and/or how long it takes for a controller of the apparatus to process raw image data, but also by the time to position the patient in the correct posture, such as e.g. the time required to direct the patient to the right place in a room and/or to instruct the patient to adopt the correct posture, e.g. on the examination table and/or in front of the X-ray imaging apparatus. Usually, the patient is guided by a radiographer, an operator and/or nurse to the correct posture, which may take some time and hence affects the patient throughput.

In some cases, increasing the patient throughput may also allow better and/or safer interventions. For example, if a very high throughput for imaging is requested, such as e.g. up to 700 patients per day on an X-Ray imaging apparatus, radiographers may take several shortcuts in order to save time and reach such high throughput. One of those shortcuts may be to acquire X-Ray images at a maximal dose in order to obtain a high quality image without having to adapt, optimize and/or minimize the dose for each patient. Further, X-ray images may be acquired without collimating the X-ray beam, which may lead to body parts of the patient being unnecessarily exposed to radiation. Moreover, patients may queue closely together so the next patients in line may already be present in the imaging room while the X-ray image of another patient is being taken. Whilst these measures save time, they may have undesirable side-effects for the patients, as they may receive more dose than would be strictly necessary for a good quality X-ray image.

Apart from these general considerations, it is expected that due to air pollution in certain countries, the number of lung diseases in these countries may increase within the next twenty years. Accordingly, e.g. regular chest check-ups by means of X-ray imaging may become a common screening measure, comparable to breast cancer screening.

SUMMARY OF THE INVENTION

It may therefore be desirable to provide for an improved, fast, efficient and/or cheap positioning procedure, diagnostic imaging procedure and/or diagnostic imaging apparatus.

This is achieved by the subject-matter of the independent claims, wherein further embodiments are incorporated in the dependent claims and the following description. It should be noted that the features which are in the following described for example with respect to the positioning system according to the first aspect of the invention may also be part of the X-ray imaging apparatus according to the second aspect of the invention and/or to the method for operating the positioning system according to the third aspect of the invention, and vice versa. In other words, any feature described in the following with respect to one aspect of the invention may be part of and/or may equally apply to any other aspect of the invention.

A first aspect of the invention relates to a positioning system for positioning a patient for diagnostic imaging, such as e.g. X-Ray imaging, computed tomography (CT) imaging, ultrasonography, magnetic resonance imaging (MRI) and/or diagnostic imaging using any other imaging modality. Apart from diagnostic imaging, the positioning system may also be used in any therapeutic system, such as e.g. radiation therapy systems. The positioning system comprises a sensor arrangement with at least one sensor configured to provide and/or output a sensor signal indicative of, representative of and/or correlating with at least one body parameter of the patient. The positioning system further comprises a controller, control circuitry and/or processor configured to determine a value of the at least one body parameter based on the sensor signal of the at least one sensor. The controller may e.g. be configured to process the sensor signal to determine the value of the body parameter and/or the controller may be configured to derive the value of the body parameter from the sensor signal. The positioning system further comprises at least one actuatable support configured to move at least one of an arm and a leg of the patient with respect to a torso of the patient, wherein the controller is configured to actuate the at least one actuatable support depending on and/or taking into account the determined value of the at least one body parameter to move at least one of the arm and the leg relative to the torso of the patient, such that the patient is guided to a posture of the patient for diagnostic imaging and/or for acquiring an image, such as e.g. an X-ray image.

The actuatable support may generally refer to a movable support that may be moved and/or actuated by the controller in dependence of and/or according to the determined value of the body parameter. Generally, the actuatable support may be configured to move one arm, both arms, both arms simultaneously, both arms separately from one another, both arms independently from one another, one leg, both legs, both legs simultaneously, both legs separately from one another, and/or both legs independently from one another. Also the head of the patient may be moved by means of the actuatable support. Further, the actuatable support may be configured to move one arm and one leg simultaneously, separately from one another and/or independently from one another. Also both arms and both legs may be moved by the actuatable support simultaneously, separately from one another and/or independently from one another. The actuatable support may comprise one or more support elements. By way of example, the actuatable support may comprise at least one support element for supporting and/or moving one or both arms of the patient. Further, the actuatable support may comprise at least one support element for supporting and/or moving one or both legs of the patient. Therein, various support elements of the actuatable support may be actuated simultaneously, synchronously, independently and/or separately.

Generally, the actuatable support may provide a rest and/or support structure for one or both arms and/or for one or both legs of the patient. By moving the actuatable support the body part of the patient arranged on the actuatable support, i.e. one or both arms and/or one or both legs, may be moved relative to the torso of the patient. Particularly, the one or both arms and/or the one or both legs of the patient may not be fixed on the actuatable support. Rather, the one or both arms and/or the one or both legs may be movably, glidingly and/or slidingly arranged on the actuatable support, such that by moving the actuatable support the patient is guided towards the posture for diagnostic imaging. In other words, a movement of the actuatable support may lead to a movement of the body part arranged thereon, which in turn may trigger a self-movement of the patient. Particularly, the one or both arms and/or the one or both legs may not be pushed and/or pulled by the actuatable support, but the actuatable support may provide a guidance to the patient for positioning and/or for self-positioning of the patient in the posture for diagnostic imaging. Accordingly, the positioning system may be regarded as a guiding system and/or a self-positioning system for the patient to take and/or adopt the posture for diagnostic imaging and/or for acquiring the image.

The movement of the actuatable support may be adjusted by the controller depending on and/or taking into account one or more values of the one or more body parameters. Therein, the movement of the actuatable support may be adjusted by the controller in direction, speed, and/or magnitude. Further, by determining one or more values of one or more body parameters, the controller may determine a morphology, a movement limitation, a mobility and/or a flexibility of the patient. Accordingly, the controller may be configured to move the actuatable support and/or to adjust the direction, speed and/or magnitude of the movement of the actuatable support e.g. depending on the patient's morphology, movement limitation, mobility and/or flexibility.

The posture for diagnostic imaging may refer to a predefined and/or correct posture of the patient suitable for a specific imaging task, such as e.g. a chest X-ray imaging task, a breast X-ray imaging task, a knee X-ray imaging task, and/or any other imaging task. Accordingly, the posture may refer to a position of the patient and/or a position of a body part of the patient to be examined in diagnostic imaging relative to a detector and/or a source of a diagnostic imaging apparatus, such as e.g. an X-ray detector and/or an X-ray source of an X-ray imaging apparatus. Therein, said position of the patient and/or said position of the body part may be suitable for acquiring an image of the patient and/or an image of said body part of the patient.

Re-phrasing the first aspect of the invention, the positioning system comprises a sensor arrangement with a sensor for determining a body parameter of the patient, wherein a value of the body parameter may be derived based on processing a sensor signal of the sensor. Based on the determined value of the body parameter, the controller may move and/or actuate the actuatable support for moving, arranging and/or orienting at least one of an arm and a leg of the patient relative to the torso, such that the entire patient and/or a body part to be examined with diagnostic imaging is positioned relative to a detector and/or a source of a diagnostic imaging apparatus, such as an X-ray imaging apparatus. Accordingly, by means of the positioning system, the patient may be semi-automatically and/or automatically guided towards the posture for diagnostic imaging. Particularly, no nurse, operator and/or radiographer may be required to bring the patient in the posture and/or the body part to be examined in the position for diagnostic imaging and/or for acquiring an image.

Accordingly, the positioning system may allow to efficiently, automatically and/or quickly bring the patient into the posture for diagnostic imaging. This may allow to acquire a high quality image, particularly without the need for re-takes of the image, as the patient may be correctly positioned. Hence, by using the positioning system a dose delivered to the patient may be reduced, as a time needed to position the patient may be reduced. Further, by means of the positioning system a throughput of an imaging apparatus may be significantly increased and costs for acquiring an image may be reduced. Apart from that, when the positioning system is integrated into an imaging apparatus, an improved, fast, efficient and/or cheap diagnostic imaging procedure may be provided.

According to an embodiment of the invention, the controller is configured to determine at least one of a morphology, a movement limitation, a mobility and a flexibility of the patient based on the determined value of the at least one parameter. The controller is configured to actuate the at least one actuatable support depending on at least one of the determined morphology, the determined movement limitation, the determined mobility and the determined flexibility of the patient.

In other words, the actuation of the at least one actuatable support by the controller may be responsive to a positioning of the patient based on the sensor arrangement and may be adjusted and/or customized for the morphology, the movement limitation, the mobility and/or the flexibility of the patient. This allows to efficiently and safely bring the patient into the posture for diagnostic imaging, e.g. without over-stretching an extremity of the patient during the positioning procedure.

According to an embodiment of the invention, the controller is configured to move the at least one actuatable support and/or to adjust the direction, speed and/or magnitude of the movement of the at least one actuatable support depending on at least one of the determined morphology, the determined movement limitation, the determined mobility and the determined flexibility.

This may allow to gently, safely and/or efficiently guide and/or position the patient, e.g. without over-stretching an extremity of the patient and/or without losing balance of the patient during the positioning procedure. According to an embodiment of the invention, the sensor arrangement comprises at least one sensor for detecting and/or determining a resistance, a mechanical resistance and/or a force exerted by the patient against a movement of the at least one actuatable support. For this purpose, the sensor arrangement may comprise e.g. a pressure sensor and/or a force sensor. Accordingly, the controller may be configured to move the actuatable support depending on, based on and/or taking into account the resistance and/or the force exerted by the patient. Hence a force-feedback may be established by the controller based on determining the resistance and/or the force exerted by the patient. Generally, this may allow to move the actuatable support in dependence of a movability, a movement limitation, and/or flexibility of the patient, such that the patient may be gently guided towards the posture for diagnostic imaging.

It is to be noted that the sensor arrangement may also comprise at least one sensor integrated into a wall stand and/or a detector plate. This sensor may e.g. detect a pressure exerted by the torso of the patient while leaning against the wall stand. In case this pressure increases and/or decreases, it may be determined that the patient may be losing balance and the actuatable support may be moved accordingly in order to compensate for the loss of balance of the patient.

According to an embodiment of the invention, the controller is configured to determine a movement limitation of at least one of the arm and the leg with respect to the torso of the patient based on the sensor signal of the at least one sensor and/or based on a sensor signal of a further sensor of the sensor arrangement. Alternatively or additionally, the controller is configured to actuate the at least one actuatable support depending on a movement limitation of at least one of the arm and the leg of the patient. By way of example, the controller may be configured to determine, based on the sensor signal, a resistance and/or a force exerted by the patient against a movement of the actuatable support and the controller may be configured to derive and/or determine the movement limitation based on the resistance and/or force exerted by the patient. Generally, this may allow to guide the patient towards the posture for diagnostic imaging taking into account a patient-specific movability, mobility, movement limitation and/or flexibility. In turn, this may allow to gently, safely and/or efficiently guide and/or position the patient, e.g. without over-stretching an extremity of the patient and/or without losing balance of the patient during the positioning procedure.

According to an embodiment of the invention, the sensor arrangement comprises at least one of a camera, a distance sensor, a laser distance sensor, an ultrasound sensor, a force sensor, a pressure sensor, and a contact sensor for detecting contact with a chin, a breast, a belly, an elbow, a hip and/or a pelvis of the patient. One or more of those sensors of the sensor arrangement may be used to directly determine one or more values of one or more body parameters, such as e.g. a height, a weight, an arm length and/or a leg length. By way of example, one or more values of one or more body parameters can be collected and/or determined via a camera, a camera system with depth information, a 3D scanner, and/or a 2D image recognition system capturing a sequence of images taken, e.g. while the patient is asked to turn himself to expose various body angles. This may allow to determine the morphology of the patient and to move the actuatable support depending on the morphology of the patient. Moreover, one or more sensors of the sensor arrangement may be used to indirectly determine one or more values of one or more body parameters. By way of example, the resistance and/or force exerted by the patient against the movement of the actuatable support may be used to indirectly determine one or more values of one or more body parameters, such as e.g. a movement limitation, a mobility and/or a flexibility of the patient and/or of a body part of the patient.

According to an embodiment of the invention, the at least one body parameter of the patient is at least one of a length of an extremity, a length of an arm, a length of a leg, a length of a neck, a belly size, a breast size, a spine shape, a movability of a body joint, a movability of a neck, a movability of a scapula, a movability of a shoulder, a movability of a knee, a movability of a hip, a movability of an ankle, a movability of a wrist, a movability of a chest, a movability of an elbow, a body height, and a corpulence. By determining one or more values of one or more of those body parameters, the patient may be guided towards the posture for diagnostic imaging taking into account the morphology, the movability, the movement limitation and/or a flexibility of the patient and/or of a body part of the patient. Accordingly, the speed, direction and/or magnitude of the movement of the actuatable support may be adjusted by the controller based and/or depending on the morphology, the movement limitation, the movability and/or flexibility of the patient. This allows to efficiently and safely bring the patient into the posture for diagnostic imaging, e.g. without over-stretching an extremity of the patient during the positioning procedure.

According to an embodiment of the invention, the at least one actuatable support comprises at least one of a handle, an arm support, an armpit support, a footrest, a leg support, and an elastic band. Therein, the handle, the arm support, the armpit support, the footrest, the leg support, and the elastic band may refer to support elements of the actuatable support. The actuatable support may comprise any combination of these support elements. Further, various of these support elements may be moved and/or actuated simultaneously, synchronously, independently and/or separately with respect to each other.

According to an embodiment of the invention, the at least one actuatable support is movable three-dimensionally and/or rotatable. The actuatable support may e.g. be rotatable around three orthogonal axes. This may allow to increase and/or enhance a geometrical flexibility of the positioning system.

According to an embodiment of the invention, the at least one actuatable support comprises at least one handle for being grasped with at least one hand of the patient, wherein the controller is configured to move the at least one handle upward, e.g. above a head of the patient, to stretch the patient and/or to move a scapula of the patient towards a spine of the patient. Generally, the at least one handle may serve to properly position one or both arms, one or both scapulae, and/or one or both shoulders of the patient. Such movement of the handle may allow to properly position the patient for capturing and/or acquiring a side X-ray image of a chest of the patient. Further, an image quality of the side X-ray image may be improved by positioning the patient in such position, because the shoulders and/or scapulae may not block a view of the lungs.

According to an embodiment of the invention, the at least one actuatable support comprises a first handle for being grasped with a first hand of the patient and a second handle for being grasped with a second hand of the patient. Therein, the first and second handles may refer to support elements of the actuatable support. Generally, the first and second handles may serve to properly position one or both arms, one or both scapulae, and/or one or both shoulders of the patient.

According to an embodiment of the invention, the controller is configured to move the first handle and the second handle upward and laterally outward in opposite directions to open the arms of the patient. Alternatively or additionally, the controller is configured to move the first handle and the second handle downward and towards a rear side of a detector, e.g. a detector plate, of a diagnostic imaging apparatus, e.g. an X-ray imaging apparatus, such that a distance between a scapula and a spine of the patient is increased. Therein, the first and second handles may be moved simultaneously or one after the other. Generally, the first and second handles may serve to properly position one or both arms, one or both scapulae, and/or one or both shoulders of the patient. Such movement of the first and second handles may allow to properly position the patient for capturing and/or acquiring a front X-ray image of a chest of the patient. Further, an image quality of the front X-ray image may be improved by positioning the patient in such position, because the shoulders and/or scapulae may not block a view of the lungs.

According to an embodiment of the invention, the positioning system further comprises a wall stand configured to encompass a detector, e.g. an X-ray detector and/or a detector plate, and configured to support the torso of the patient. The positioning system further comprises at least one alignment element for aligning a vertical axis of the patient and a center axis of the detector based on moving and/or guiding the torso of the patient towards a center axis of the wall stand, e.g. by actuating the alignment element with the controller. By way of example, the at least one alignment element may refer to two clamps arranged on two opposite sides of the wall stand and/or of the detector. The clamps may be initially open and, once the patient is arranged between the clamps, the clamps may be moved towards each other to center the torso with respect to the detector and/or to align the vertical axis and the center axis. Further, the wall stand may comprise a morphing surface that may serve as alignment element, wherein the morphing surface may deform in contact with the patient's torso to adopt a body shape of the patient and at the same time guide the patient towards the center of the wall stand to align the vertical axis and the center axis.

According to an embodiment of the invention, the positioning system further comprises a pivotable support for supporting a foot, feet, a back and/or a buttocks of the patient. Specifically, the pivotable support may be configured for supporting the patient in an upright position. Therein, the controller is configured to actuate the pivotable support such that the torso of the patient is moved towards a wall stand of the positioning system and/or towards a detector of a diagnostic imaging apparatus, e.g. an X-ray imaging apparatus. Generally, moving the patient's torso towards the wall stand may allow to bring the torso closer to the detector that may be arranged in the wall stand. This may also increase a quality of the acquired image. By way of example, the pivotable support may refer to a stand and/or a baseplate, on which the patient may be standing. Alternatively or additionally, the pivotable support may refer to a pivotable stool supporting the buttocks of the patient. By pivoting the pivotable support the torso of the patient may be moved towards the wall stand such that the patient may lean against the wall stand.

According to an embodiment of the invention, the positioning system further comprises at least one instructing element for providing an acoustic, visual, audio-visual, and/or haptic instruction to the patient to guide the patient to the posture for diagnostic imaging. Generally, the patient may be directed to the posture and/or instructed to move itself to the posture for image acquisition by means of the instructing element. Also, the patient may be instructed e.g. to change positions according to the imaging task. For instance, the patient may be instructed to turn and/or move from a position for acquiring a front chest X-ray image to a position for acquiring a side chest X-ray image. By way of example, the at least one instructing element may comprise a speaker for acoustically instructing the patient, a light element providing visual guidance and/or at least one screen providing visual guidance. For instance, by using one or more values of one or more body parameters of the patient a personalized avatar may be created and displayed on the screen to show the correct positioning steps to the patient during the imaging procedure. Also, a real-time representation of the patient superimposed onto the virtual avatar may be displayed on the screen that allows the patient to mimic the avatar's posture and actions. Further, a haptic signal may be provided to the patient, e.g. by means of a vibrating element arranged on the actuatable support. Accordingly, by means of the instructing element, the patient may be quickly, automatically and/or efficiently guided towards the posture.

A second aspect of the invention relates to an X-ray imaging apparatus comprising an X-ray source, an X-ray detector, and a positioning system as described above and in the following. Particularly, the X-ray imaging apparatus may be configured for chest X-ray imaging. Therein, the X-ray detector may refer to a detector plate that may e.g. be arranged in a wall stand of the positioning system.

A third aspect of the invention relates to a method for operating the positioning system, as described above and in the following, to position a patient for diagnostic imaging. The method may also refer to a method for positioning a patient for diagnostic imaging and/or to a method for operating an imaging apparatus with a positioning system. The method comprises the steps of:

processing, with a controller of the positioning system, a sensor signal of a sensor of the positioning system;

determining, with the controller, a value of at least one body parameter based on the sensor signal; and actuating, with the controller, at least one actuatable support of the positioning system, the actuatable support being configured to move at least one of an arm and a leg of the patient with respect to a torso of the patient, wherein the actuatable support is actuated in dependence of the determined value of the at least one body parameter, such that the patient is guided to a posture for diagnostic imaging based on moving at least one of the arm and the leg relative to the torso.

A fourth aspect of the invention relates to a computer program element, which, when executed on a controller of a positioning system, instructs the positioning system to carry out the steps of the method as described above and in the following.

A fifth aspect of the invention relates to a computer-readable medium on which a computer program element is stored which, when executed on a controller of a positioning system, instructs the positioning system to carry out the steps of the method as described above and in the following.

These and other aspects of the invention will be apparent from and elucidated with reference to the embodiments described hereinafter.

BRIEF DESCRIPTION OF THE DRAWINGS

The subject-matter of the invention will be explained in more detail in the following with reference to exemplary embodiments which are illustrated in the attached drawings, wherein.

In principle, identical or like parts are provided with identical or like reference symbols in the Figs.

DETAILED DESCRIPTION OF EMBODIMENTS

Figure 1:
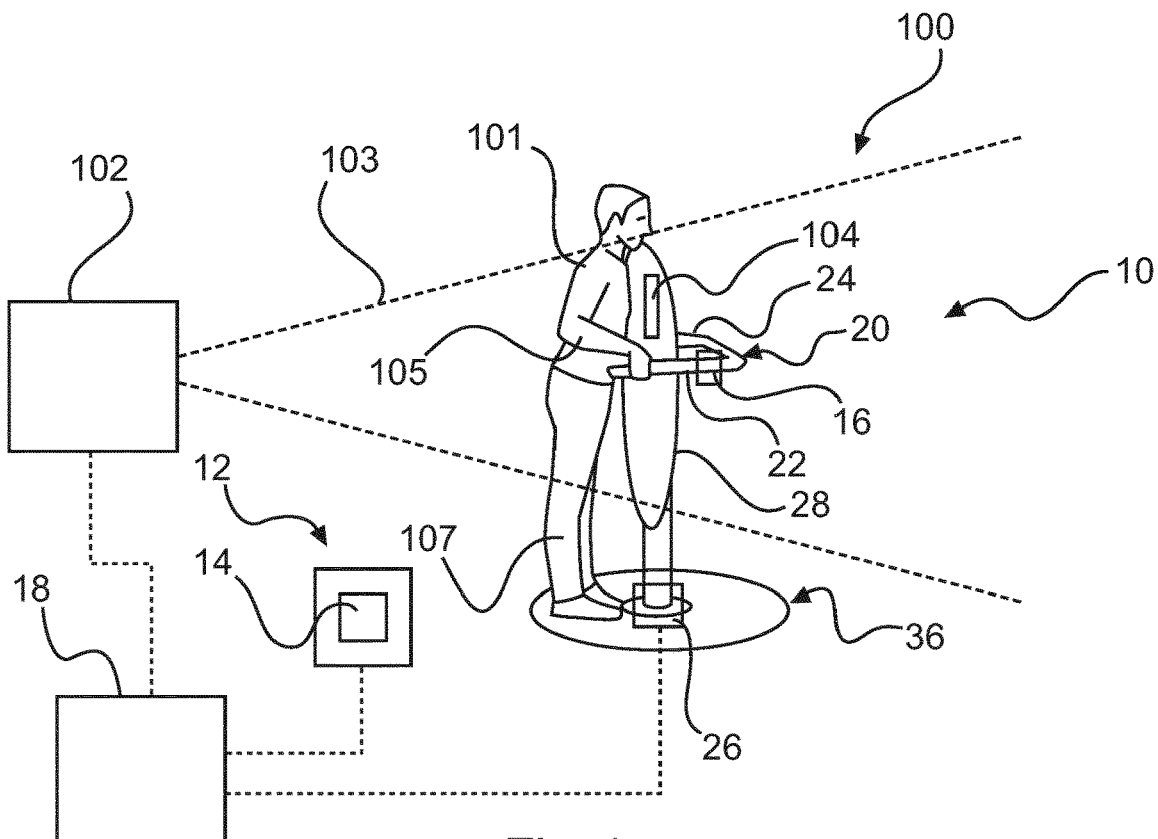
FIG. 1 shows schematically an X-ray imaging apparatus according to an exemplary embodiment of the invention.

FIG. 1 shows schematically an X-ray imaging apparatus 100 according to an exemplary embodiment of the invention.

The X-ray imaging apparatus 100 of FIG. 1 is a chest X-ray imaging apparatus 100, wherein a patient 101 is depicted in a posture for acquiring a front chest X-ray image. However, the X-ray imaging apparatus 100 may alternatively or additionally be designed for acquiring an X-ray image of any other body part of the patient 101.

The X-ray imaging apparatus 100 comprises an X-ray source 102 for emitting a beam 103 of X-ray particles and/or X-ray photons towards the patient 101. The X-ray source 102 may be any type of X-ray source, such as an X-ray tube, a stereo X-ray tube or the like.

The X-ray imaging apparatus 100 further comprises an X-ray detector 104 for detecting X-ray particles that passed through the patient 101. The detector 104 may be a detector plate 104. E.g. the detector 104 may comprise a scintillation device optically coupled to one or more detecting elements, such as e.g. photodiodes.

The X-ray imaging apparatus 100 further comprises a positioning system 10 for positioning the patient 101 for the acquisition of the X-ray image. The positioning system 10 may specifically be configured to guide the patient 101 towards and/or into a posture for diagnostic imaging and/or for acquiring the X-ray image.

The positioning system 10 comprises a sensor arrangement 12 having at least one sensor 14, 16 for detecting at least one body parameter of the patient 101 and/or for outputting one or more sensor signals indicative of one or more body parameters. The one or more sensor signals are output and/or provided to a controller 18 of the positioning system 10 that processes the one or more sensor signals to determine and/or derive at least one value of the at least one body parameter.

The positioning system 10 further comprises at least one actuatable support 20 configured to move at least one of an arm 105 and a leg 107 of the patient 101 relative to a torso of the patient 101. Therein, the at least one actuatable support 20 is actuated by the controller 18 in dependence of and/or taking into account the determined at least one value of the at least one body parameter, such that the patient 101 is guided towards the posture for image acquisition by moving at least one of the arm 105 and the leg 107 relative to the torso of the patient 101, as will be further described in the following.

In the example depicted in FIG. 1, the at least one actuatable support 20 comprises a first handle 22 for being grasped with a first hand of the patient 101 and a second handle 24 for being grasped with a second hand of the patient. Therein, the first handle 22 and the second handle 24 may be moved three-dimensionally and/or each may be rotated around three orthogonal axes.

To actuate and/or move the actuatable support 20, the controller 18 is coupled to an actuator 26 configured to move and/or rotate the actuatable support 20, i.e. the first and second handles 22, 24. The actuator 26 may be any kind of actuator 26, such as e.g. an electrical motor and/or a pneumatic actuator.

Generally, the sensor arrangement 12 may serve to determine, based on the at least one body parameter, a morphology, movability, flexibility and/or a movement limitation of the patient 101. Therein, the at least one body parameter may be at least one of a length of an extremity, a length of an arm, a length of a leg, a length of a neck, a belly size, a breast size, a spine shape, a movability of a body joint, a movability of a neck, a movability of a scapula, a movability of a shoulder, a movability of a knee, a movability of a hip, a movability of an ankle, a movability of a wrist, a movability of a chest, a movability of an elbow, a body height, and a corpulence.

In order to determine the at least one body parameter, the sensor arrangement 12 may comprise at least one of a camera, a distance sensor, a laser distance sensor, an ultrasound sensor, a force sensor, a pressure sensor, and a contact sensor for detecting contact with a chin, a breast, a belly, an elbow, a hip and/or a pelvis of the patient 101.

In the exemplary embodiment shown in FIG. 1, the sensor arrangement 12 comprises a camera 14 for visually detecting the patient 101 and/or for visually determining at least one body parameter and/or for visually determining the morphology of the patient 101. The sensor 14 and/or the sensor arrangement 12 outputs the sensor signal to the controller 18 that processes the sensor signal of sensor 14 and determines one or more visually detectable body parameters of the patient 101, such as e.g. a height, a width, a length of an arm, a length of a torso, a width of the torso, a length of a leg, a shape of a spine, a belly size, a breast size, and/or any other visually detectable body parameter of the patient 101.

The further sensor 16 of the sensor arrangement 12 is configured to determine and/or detect a resistance and/or a force exerted by the patient 101 against a movement of the actuatable support 20, the first handle 22 and/or the second handle 24. By way of example, sensor 16 may be or comprise a pressure sensor and/or a force sensor. The further sensor 16 outputs a further sensor signal to the controller 18, and the controller 18 processes the further sensor signal to determine a movement limitation of the patient 101, such as e.g. a movement limitation of the arms 105 of patient 101.

The sensor arrangement 12 may comprise one or more further sensors 14a to 14e (see FIGS. 3A and 3B) in order to detect one or more further body parameters and/or to detect a movement limitation of a further body part of the patient 101. This way, the controller 18 may be enabled to comprehensively determine the morphology as well as the movability, flexibility and/or movement limitations of the patient 101.

The positioning system 10 further comprises a wall stand 28 that encompasses and/or surrounds the X-ray detector 104. During image acquisition, the patient 101 should lean against the wall stand 28 in order to bring the chest as close as possible to the X-ray detector and thus improve image quality. Further, by leaning against the wall stand 28 the patient 101 may keep the posture, into which the patient 101 has been guided by means of the positioning system 10, during image acquisition.

As in the correct posture for frontal chest X-ray imaging, the torso should lean against the wall stand 28, the positioning system 10 further comprises a pivotable support 36 supporting the feet and/or a foot of the patient 101 in an upright position of the patient 101. In the example shown in FIG. 1, the pivotable support comprises and/or is a pivotable baseplate 36, on which the patient 101 is standing in an upright position. The controller 18 can actuate the pivotable support 36 to move and/or pivot the pivotable support 36 towards the wall stand 28, and hence to move the torso of the patient 101 towards the wall stand 28. Accordingly, the pivotable support 36 may be a balancing stool to guide and/or push the patient's torso towards the wall stand 28 and/or detector 104. By way of example, the patient 101 can be asked to stand on the pivotable support 36 and/or baseplate 36 just in front of the detector 104 and/or wall stand 28. The baseplate 36 can then slightly pivot to push the patient 101 towards the detector 104. In this way, it may be ensured that the patient's torso is in contact with the wall stand 28.

In the following figures, operation of the positioning system 10 will be explained in more detail.

Figure 2A:
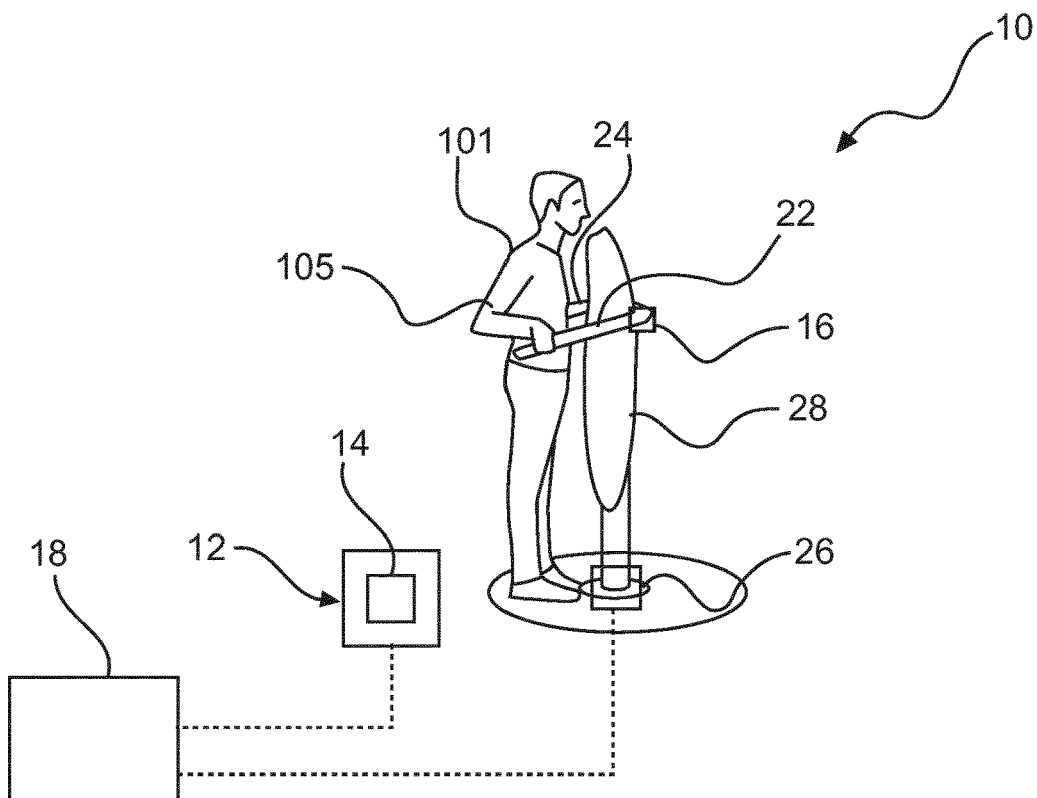
FIGS. 2A to 2G each show schematically a positioning system according to an exemplary embodiment of the invention.
Figure 2B:
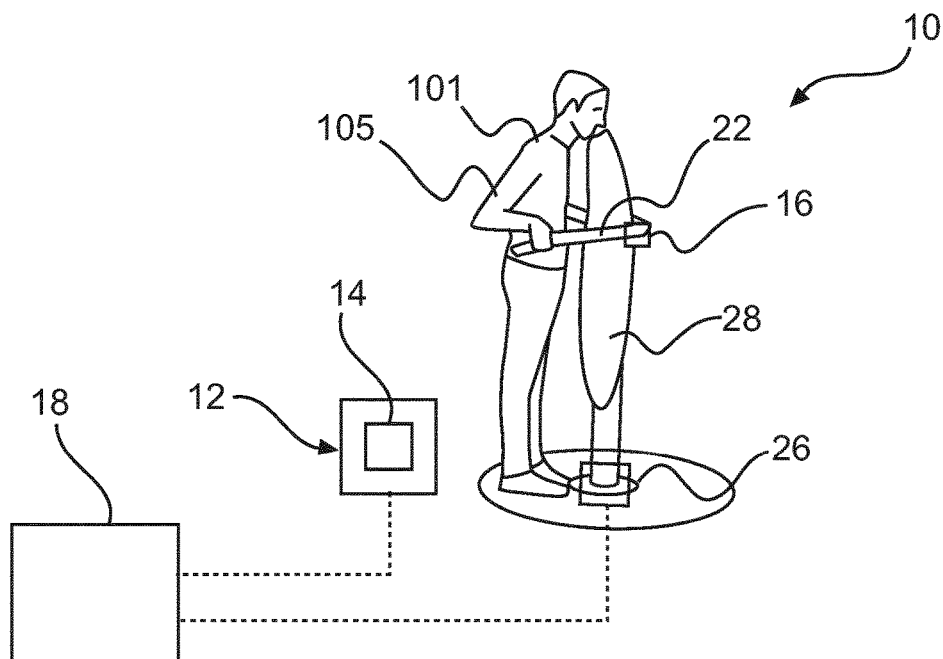
Figure 2C:
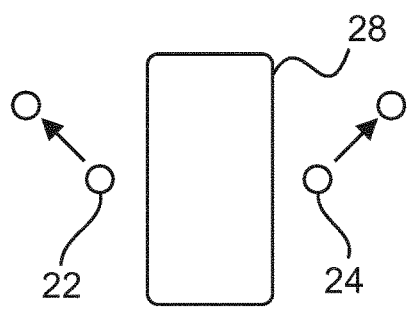
Figure 2D:
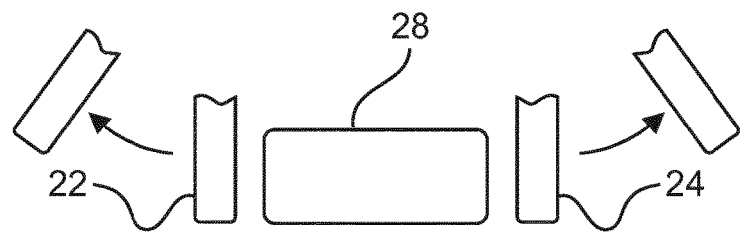
Figure 2E:
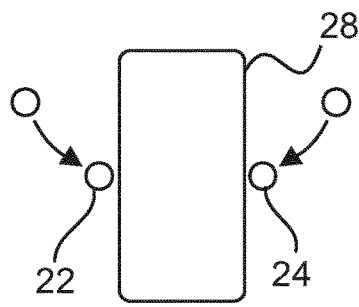
Figure 2F:
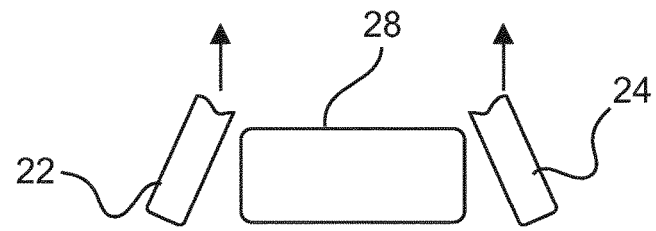
Figure 2G:
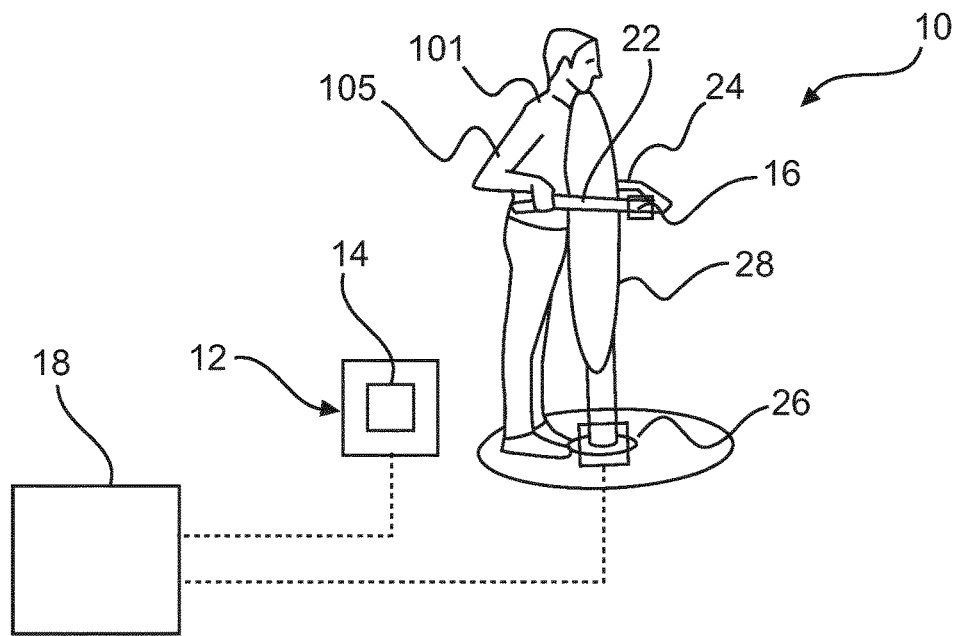

FIGS. 2A to 2G each show a positioning system 10 according to an exemplary embodiment of the invention. Specifically, FIGS. 2A to 2G illustrate an actuation and/or movement of the actuatable support 20 during operation of the positioning system 10. Therein, FIG. 2A illustrates an initial position of the patient 101 before image acquisition, FIG. 2G illustrates the patient 101 in another position similary to a posture for diagnostic imaging and/or for acquiring the X-ray image, and FIGS. 2B to 2F illustrate the movement of the actuatable support 20 to guide the patient 101 towards the final position and/or posture as illustrated in FIG. 2G. Specifically FIGS. 2C and 2E each show a front view of a part of the positioning system 10, and FIGS. 2D and 2F each show a top view of a part of the positioning system 10. If not stated otherwise, the positioning system 10 shown in FIGS. 2A to 2G comprises the same features, functions and/or elements as the positioning system 10 of FIG. 1.

Figure 4:
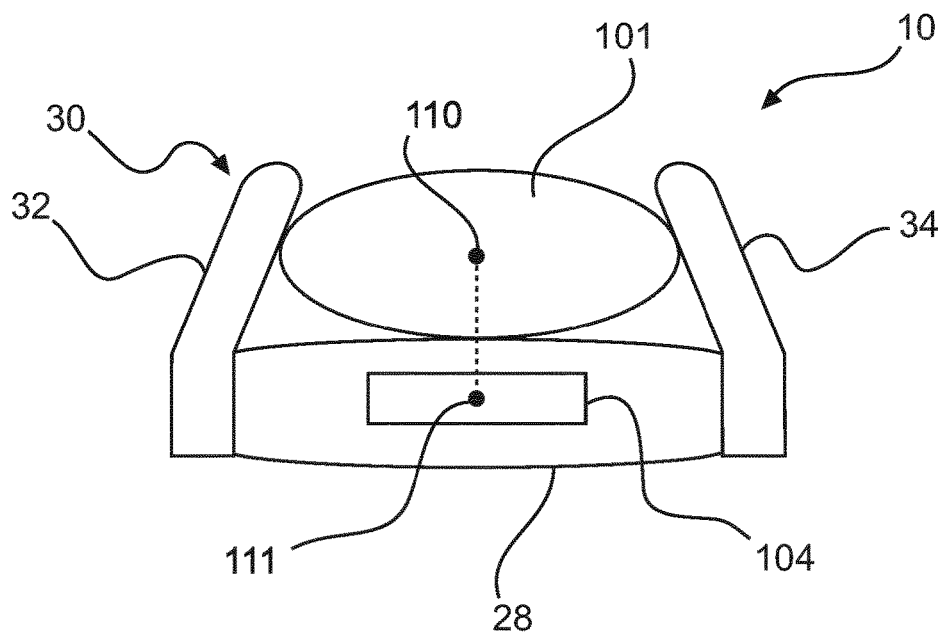
FIG. 4 shows schematically a part of a positioning system according to an exemplary embodiment of the invention.

In FIG. 2A to 2G the patient 101 is guided into the posture for acquiring a frontal chest X-ray image. For this purpose, the shoulders and/or scapulae of the patient 101 should not block the view of the lungs and/or should be moved as far as possible away from the spine of the patient 101. Accordingly, the shoulders and/or scapulae should be moved out of the way. For a frontal chest X-ray image, it may be favorable to roll the shoulders towards the detector 104 and/or towards the wall stand 28. For a side chest X-ray image, it may be favorable to move the arms 105 above the shoulders to pull the shoulders and/or scapulae up, as described with reference to FIG. 6. Apart from that, it may be favorable to align a vertical axis of the patient 101 with a center axis of the detector 104, as illustrated in FIG. 4. Also, it may be favorable that a chin of the patient 101 lies on the wall stand 28 and/or an upper surface thereof, as e.g. shown in FIG. 2G.

In order to guide the patient 101 into the posture for diagnostic imaging and/or for acquiring the X-ray image, the patient may be asked to grab the first and second handles 22, 24 with its arms 105 and/or to lay its arms 105 down on the first and second handles 22, 24 of the actuatable support 20, as shown in FIG. 2A.

The sensors 14, 16 may then be operated by the controller 18 to provide sensor signals indicative of one or more body parameters and the controller 18 may derive one or more values of the one or more body parameters from the sensor signals, as described with reference to FIG. 1.

The movement of the actuatable support 20 and/or the first and second handles 22, 24 may be adjusted by the controller 18 depending on the one or more values of the one or more body parameters. Therein, the movement may be adjusted in direction, speed, and/or magnitude, e.g. depending on the patient's morphology, as determined and/or described by the body parameters, such as the length of the arms, a movability of an elbow, a movability of a joint or the like. Apart from that, movement limitations of the patient 101 as detected with sensors 14, 16 and/or determined with controller 18 may be taken into account when moving the actuatable support 20. Such movement limitations may be determined by means of a camera-based sensor 14, e.g. with a movement analysis of a series of captured optical images. This may be done prior to and/or during the imaging procedure. Further, movement limitations may be determined by means of sensor 16, as described with reference to FIG. 1, based on determining the resistance and/or force exerted by the patient 101 against the movement of the actuatable support 20. Sensor 16 may for this purpose e.g. be arranged in the first and/or second handles 22, 24 to measure the force needed to guide the patient's 101 arms.

As illustrated in FIGS. 2C (front view) and 2D (top view), to bring the patient 101 into the correct posture, the controller 18 actuates the actuatable support 20 such that the first and second handles 22, 24 are moved upward towards a head of the patient 101 and/or towards a top of the wall stand 28, as indicated by the arrows in FIG. 2C. Further, the controller 18 actuates the actuatable support 20 such that the first and second handles 22, 24 are laterally moved outwards in opposite directions in order to open up the arms of the patient 101, as indicated by the arrows in FIG. 2D. Both movements may be performed simultaneously or one after the other.

Referring to FIGS. 2E (front view) and 2F (top view), the controller 18 actuates the actuatable support 20 such that the first and second handles 22, 24 describe a motion downward and towards the rear side of the wall stand 28 and/or the detector 104 to increase a distance between the scapulae and the spine. Both movements may be performed simultaneously or one after the other. In other words, the first and second handles 22, 24 may bring the hands of the patient 101 on the back of the detector 104 and/or wall stand 28, e.g. in order to have the patient 101 "hug" the detector 104 and/or wall stand 28.

By moving the first and second handles 22, 24, the patient's arms are moved relative to the torso and the patient 101 is gently guided towards the posture depicted in FIG. 2G without pulling, pushing and/or forcing the patient 101 into this posture, but rather by instructing the patient 101 to position itself. By using the positioning system 10, no operator, nurse and/or radiographer is required for positioning the patient 101. Rather, the patient 101 is automatically positioned and/or self-positioned by the positioning system 10.

Figure 3A:
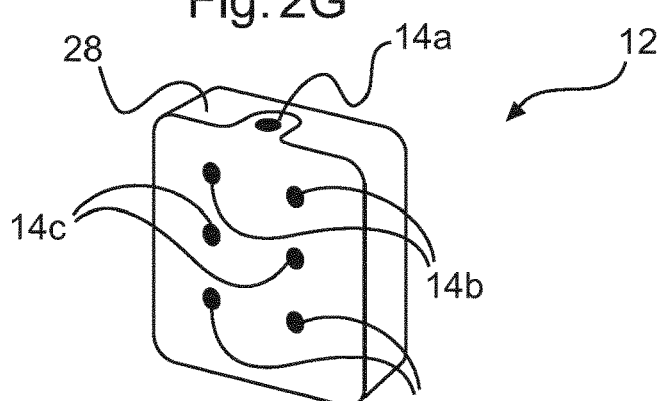
FIGS. 3A and 3B each show schematically a part of a positioning system according to an exemplary embodiment of the invention.
Figure 3B:
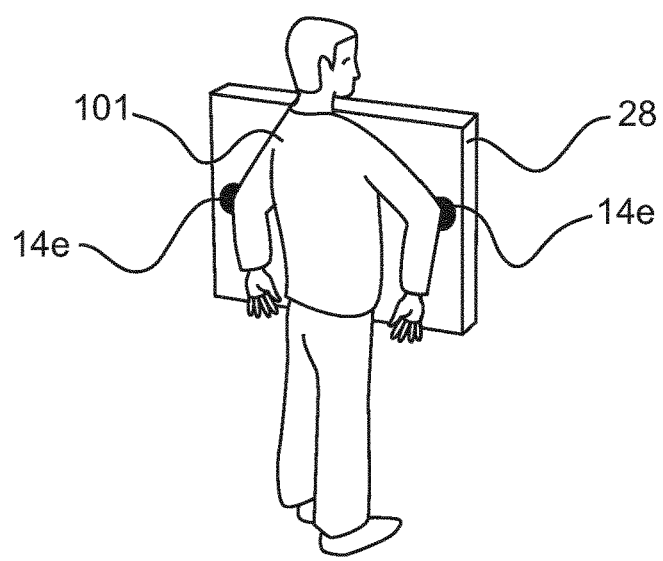

FIGS. 3A and 3B each show schematically a part of a positioning system 10 according to an exemplary embodiment of the invention. If not stated otherwise, the positioning system 10 shown in FIGS. 3A and 3B comprises the same features, functions and/or elements as the positioning system 10 of FIGS. 1 to 2G.

FIG. 3A shows a perspective view of a wall stand 28 of the positioning system 10, in which various sensors 14a to 14d are arranged that are part of the sensor arrangement 12. The sensors 14a to 14d may be contact sensors for determining contact with a chin, a breast, a belly and/or a torso of the patient 101. The sensors 14a to 14d may e.g. be pressure sensors.

Specifically, a chin sensor 14a is arranged on a top part of the wall stand 28 to detect when the chin of the patient 101 is in its correct position.

Moreover, at various heights of the wall stand, sensors 14b to 14d are arranged pairwise to detect contact with the belly, breast and/or torso of the patient 101. Therein, sensor pair 14b is configured to detect contact with the breast and sensor pair 14d is configured to detect contact with the belly. By processing the sensor signals of the sensors 14b to 14d and by evaluating differences between the signals, a breast size, belly size and/or a relative size between breast and belly may be determined. The determined sizes of the breast and belly can then be taken into account by the controller 18 when guiding the patient 101 into the posture. Note that depending on the patient 101, for some patients the breast will touch the wall stand but not the belly, while for others it will be the contrary.

FIG. 3B illustrates a patient 101 in the posture for image acquisition.

The wall stand 28 depicted in FIG. 3B further comprises a pair of sensors 14*e* to detect contact with the elbows of the patient 101. This may signal that correct posture for a frontal chest X-ray image has been taken by the patient 101. Contact with one or more of the sensor pair 14*e* may trigger image acquisition.

The sensors 14*e* can detect the elbows touching the wall stand 28, which indicates that the shoulders have been properly rolled forwards. An advantage may be that these sensors 14 can be positioned outside of the imaging area of the wall stand 28.

Alternatively or additionally to pressure sensors 14*a* to 14*e*, a conductive lacquer can be added to the surface of the wall stand 28 to get information on the patient position (similarly to turning the surface into a "touch screen").

FIG. 4 shows schematically a part of a positioning system 10 according to an exemplary embodiment of the invention. If not stated otherwise, the positioning system 10 shown in FIG. 4 comprises the same features, functions and/or elements as the positioning system 10 of FIGS. 1 to 3B.

In FIG. 4 a schematic top view of a wall stand 28, a detector 104 and a patient 101 is shown.

The positioning system 10 shown in FIG. 4 comprises an alignment element 30 for moving the torso of the patient towards the center of the wall stand 28 and/or the detector 104, in order to align a vertical axis 110 of the patient 101 with a center axis 111 of the detector 104. The torso may be moved such that the axes 110, 111 are arranged parallel and such that the vertical axis of the patient 101 is centered with respect to the wall stand 28 and/or the detector 104.

The alignment element 30 comprises a first clamp 32 and a second clamp 34 arranged on opposite sides of the wall stand 28 and/or the detector 104. Initially the clamps 32, 34 may be spaced apart from each other and/or may be open. If the patient 101 is arranged between the first clamp 32 and the second clamp 34, the clamps 32, 34 may be moved towards each other to gently guide the patient's torso towards a centered position, in which the axes 110, 111 are aligned and the torso is centered with respect to the wall stand 28.

Alternatively or additionally, the detector 104 and/or an outer surface of the wall stand 28 may be morphable and/or deformable, such that it deforms in contact with the patient 101 to adopt its body shape and at the same time guide the patient 101 towards the center of the wall stand 22.

Figures 5A, 5B:
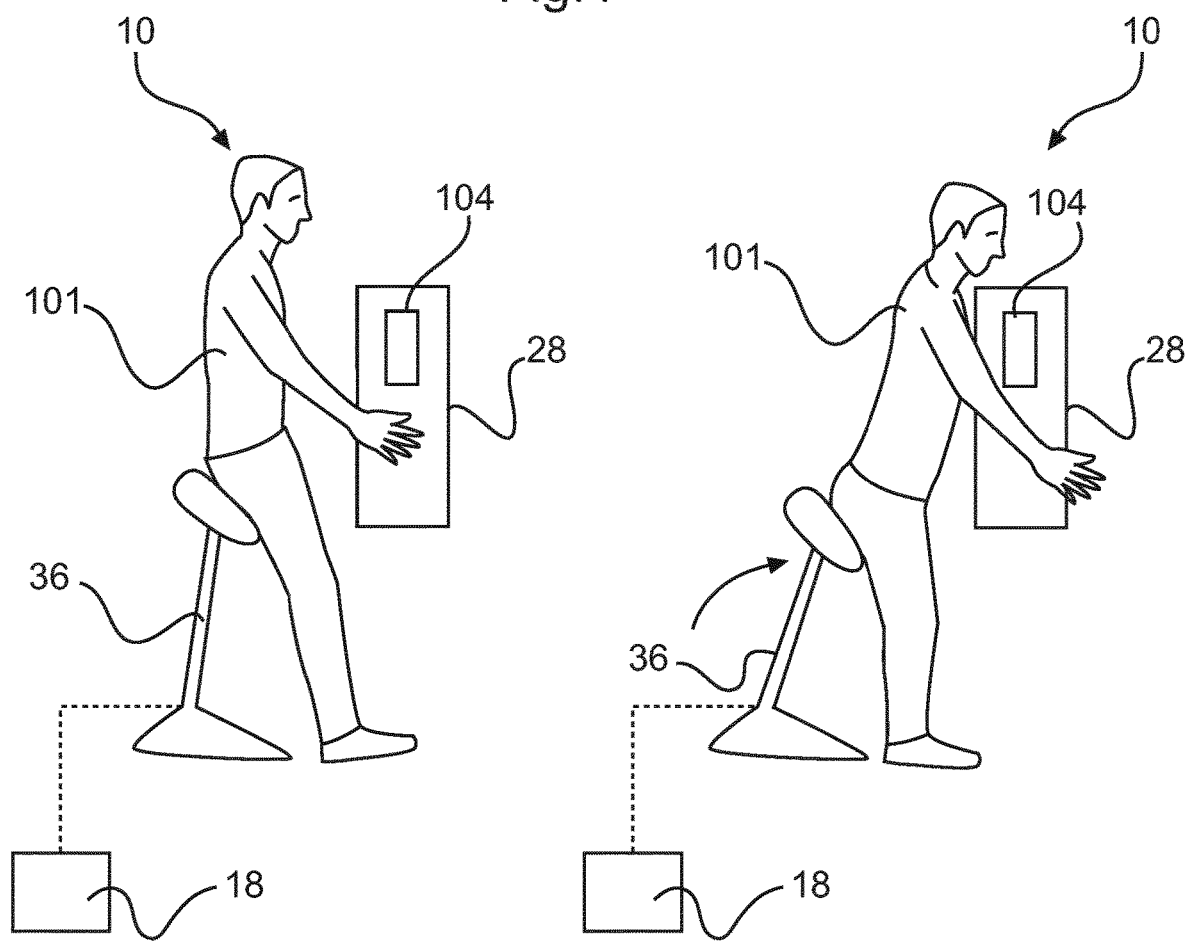
FIGS. 5A and 5B each show schematically a part of a positioning system according to an exemplary embodiment of the invention.

FIGS. 5A and 5B each show schematically a part of a positioning system 10 according to an exemplary embodiment of the invention. If not stated otherwise, the positioning system 10 shown in FIGS. 5A and 5B comprises the same features, functions and/or elements as the positioning system 10 of FIGS. 1 to 4.

The positioning system 10 of FIGS. 5A and 5B comprises a pivotable support for supporting a buttocks and/or a back of the patient 101 in an upright position of the patient 101. As in the correct posture for frontal chest X-ray imaging, the torso should lean against the wall stand 28, the controller 18 can actuate the pivotable support 36 to move and/or pivot the pivotable support 36 towards the wall stand 28, and hence to move the torso of the patient 101 towards the wall stand 28, as indicated by the arrow in FIG. 5B. Accordingly, the pivotable support 36 may be a balancing stool to guide and/or push the patient's torso towards the wall stand 28 and/or detector 104. By way of example, the patient 101 can be asked to sit and/or lean on the pivotable support 36 and/or stool 36 just in front of the detector 104 and/or wall stand 28. The stool 36 can then slightly pivot to push the patient 101 towards the detector 104. In this way, it may be ensured that the patient's torso is in contact with the wall stand 28 and is also well centered.

Figure 6:
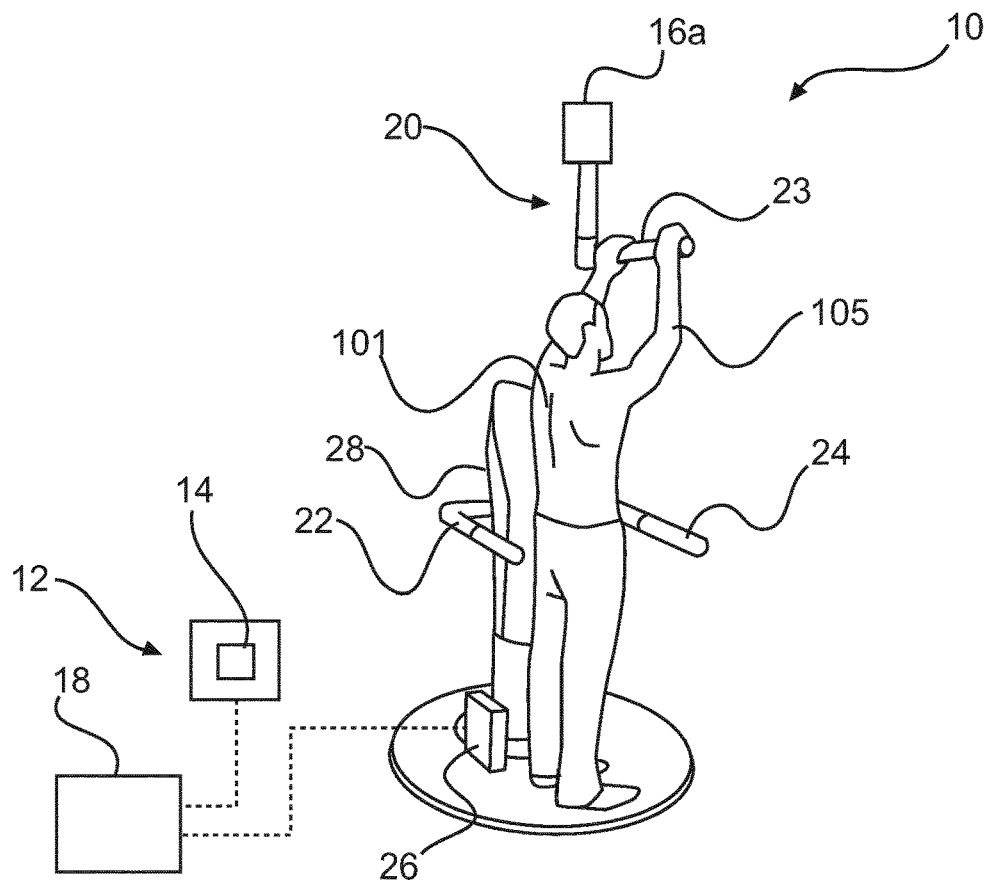
FIG. 6 shows schematically a positioning system according to an exemplary embodiment of the invention.

FIG. 6 shows schematically a positioning system 10 according to an exemplary embodiment of the invention. If not stated otherwise, the positioning system 10 shown in FIG. 6 comprises the same features, functions and/or elements as the positioning system 10 of FIGS. 1 to 5B. In the example depicted in FIG. 6, the patient 101 is guided to a posture for acquiring a side chest X-ray image. For a side chest X-ray image, it may be favorable to move the arms 105 above the shoulders to pull the shoulders and/or scapulae up.

The positioning system 10 of FIG. 6 comprises an actuatable support 20 with a first handle 22 and a second handle 24 for guiding the patient 101 to a posture for a front chest X-ray image.

The actuatable support comprises a further handle 23 arranged above the head of the patient 101 for positioning the patient 101 in a posture suitable for a side chest X-ray image. The patient may e.g. be requested to grab the further handle 23 above its head.

The controller 18 may then operate the sensors 14, 16*a* to determine one or more values of one or more body parameters, as described with reference to previous Figs. Therein, sensor 16*a* may correspond to sensor 16 as described in previous Figs.

The controller 18 may then actuate the actuator 26 to move the further handle 23 upward above the head of the patient 101 to stretch the arms 105 of the patient 101 and/or to move the scapulae upward and/or towards the spine of the patient 101.

Figure 7A:
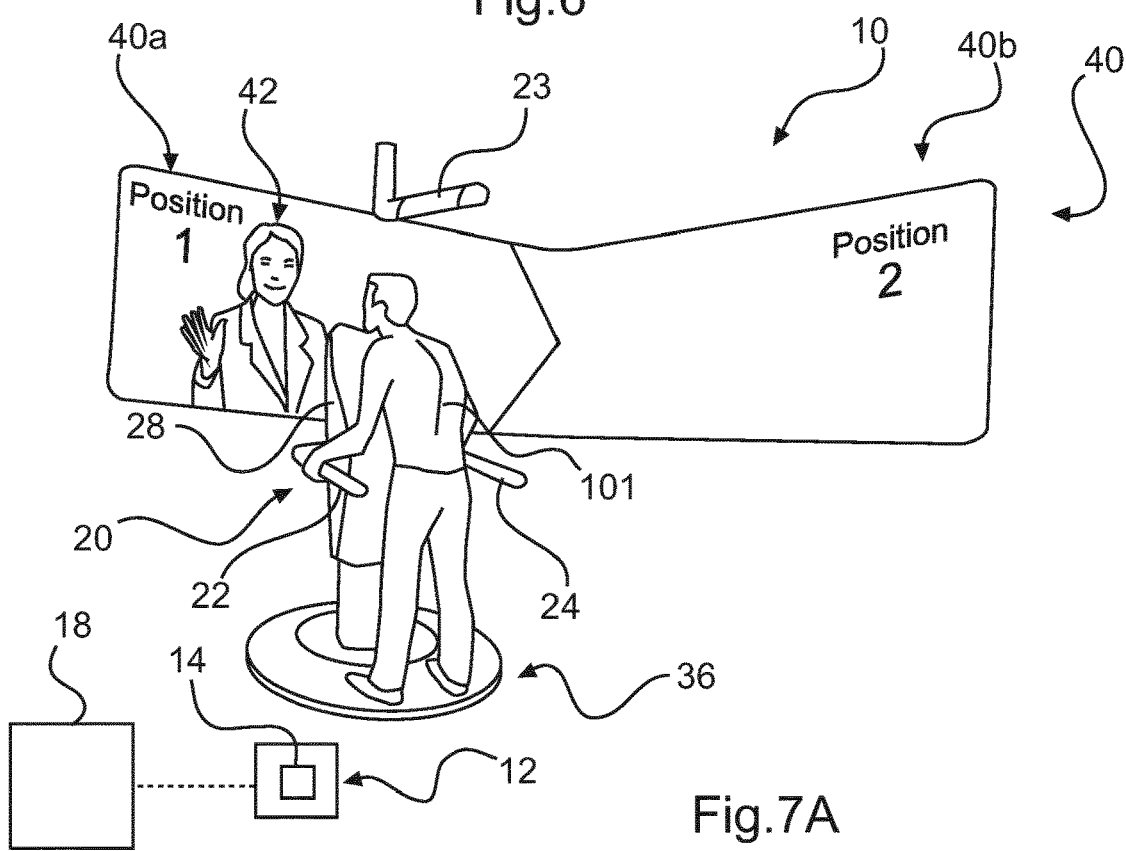
FIGS. 7A to 7C each show schematically a positioning system according to an exemplary embodiment of the invention.
Figure 7B:
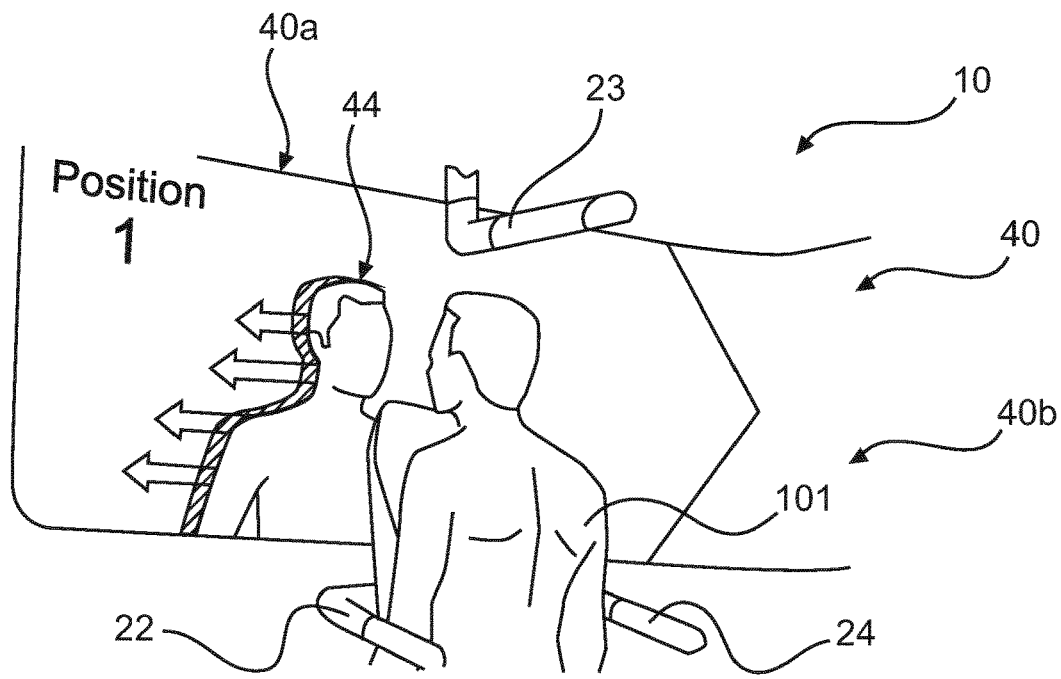
Figure 7C:
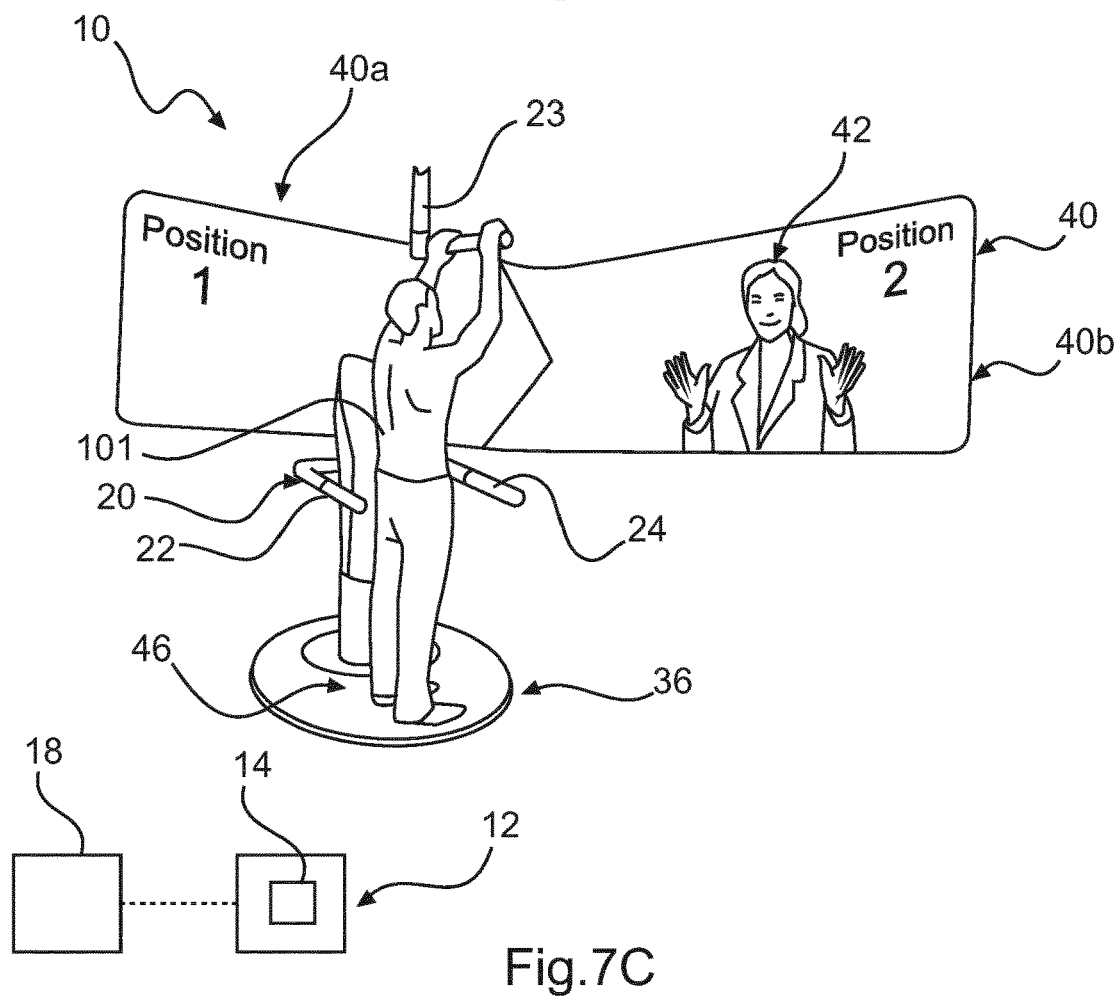

FIGS. 7A to 7C each show schematically a positioning system 10 according to an exemplary embodiment of the invention. If not stated otherwise, the positioning system 10 shown in FIGS. 7A to 7C comprises the same features, functions and/or elements as the positioning system 10 of FIGS. 1 to 6.

The positioning system 10 shown in FIGS. 7A to 7C comprises an instructing element 40 for providing an acoustic, visual and/or audio visual instruction to the patient 101 to guide the patient 101 to the posture for diagnostic imaging. Instructing element 40 is designed as a video screen 40 arranged on a wall of an imaging room.

The screen 40 comprises a first screen section 40*a* facing the patient 101 during front chest X-ray imaging and a second screen section 40*b* facing the patient 101 during side chest X-ray imaging.

The instructing element 40 comprises a guiding character 42 and/or avatar 42, e.g. a virtual nurse 42, displayed on the instructing element 40. The avatar 42 can walk from one screen section 40*a*, 40*b* to another screen section 40*a*, 40*b* to engage the patient 101 to turn along and rotate his body clockwise, e.g. by 90 degrees, to change between the postures for front and side chest X-ray imaging. The transition between the two screen section 40*a*, 40*b* can be seamless by e.g. fading out, or by connecting the two screen sections 40*a*, 40*b* with a corner display element. Alternatively, projection, holograms and/or augmented reality can be used.

The guiding character's 42 face may be arranged at a height that is slightly higher than the patient's 101 face so that the patient 101 may look upward during the guidance and rises its chin up. The avatar 42 can even move up during the instructions to make the patient 101 rise further its chin. The avatar 42 may provide a real-time, customized guidance for patient self-positioning relative to the detector 104, e.g. by using the one or more values of the one or more body parameters of the patient 101 as determined by means of the controller 18 and the sensor arrangement 12.

As illustrated in FIG. 7A the avatar 42 may acoustically, visually and/or audio-visually instruct the patient 101 to turn its face towards the avatar 42 in order to guide the patient into the posture for front chest X-ray imaging. The avatar 42 may also instruct the patient 101 to grab the first handle 22 and the second handle 24.

As illustrated in FIG. 7B, a virtual representation 44 of the patient 101 may be created based on the determined one or more values of the one or more body parameters. The virtual representation 44 may be superimposed onto the virtual avatar 42 on the instructing element 40 that allows the patient 101 to mimic the avatar's 42 posture and actions. Also, further guidance may be provided, e.g. by displaying arrows in the instructing element 40. Therein, the virtual representation 44 may be regarded as a mirror image of the patient 101, and the patient 101 may be instructed to move in the direction of the arrows until the virtual representation 44 aligns with a shadow of the virtual representation 44, which shadow may illustrate the correct posture.

The patient 101 may then be further guided into the correct posture by actuating and/or moving the actuatable support 20, as described in previous Figs.

As shown in FIG. 7C, after the front chest X-ray image has been taken, the patient 101 may be guided to the posture for a side chest X-ray image. The avatar 42 may for this purpose move from the first screen section 40a to the second screen section 40b and may ask the patient 101 to turn by about 90 degrees. The patient 101 may then be asked to grab the further handle 23 and the controller may actuate the further handle 23 to bring the patient 101 into the correct posture for the side chest X-ray image.

The positioning system 10 may comprise a further instructing element 46 that may e.g. be an illuminated area on a floor indicating a correct position of the feet of the patient. Also, a haptic instructing element may be arranged on one or more of the handles 22, 23, 24 for providing haptic instructions to the patient 101.

Figure 8:
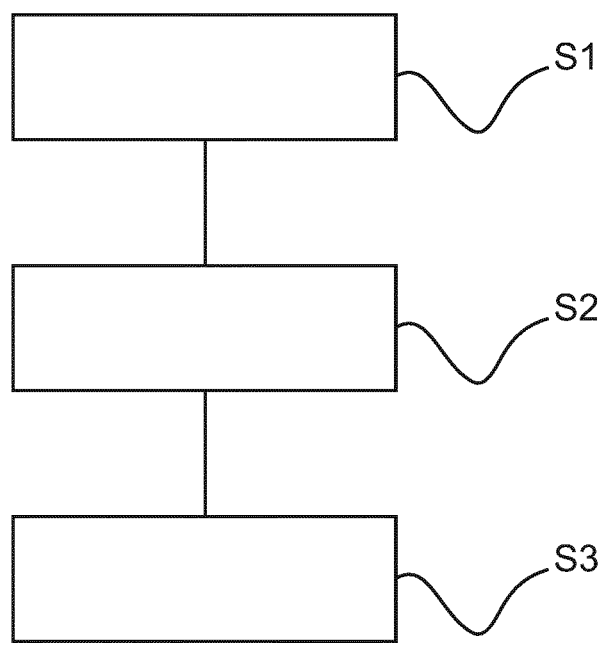
FIG. 8 shows a flow chart illustrating steps of a method for operating a positioning system according to an exemplary embodiment of the invention.

FIG. 8 shows a flow chart illustrating steps of a method for operating a positioning system 10 according to an exemplary embodiment of the invention. If not stated otherwise, the positioning system 10 comprises the same features as the positioning systems 10 described with reference to previous Figs.

In a first step S1 a sensor signal of a sensor 14, 16 of the positioning system 10 is processed with a controller 18. In a second step S2 the controller 18 determines a value of at least one body parameter based on the sensor signal. In a third step S3 the controller 18 actuates at least one actuatable support 20 of the positioning system 10, the actuatable support 20 being configured to move at least one of an arm 195 and a leg 107 of the patient 101 with respect to a torso of the patient 101. Therein, the actuatable support 20 is actuated in dependence of the determined value of the at least one body parameter, such that the patient 101 is guided to a posture for diagnostic imaging based on moving at least one of the arm 105 and the leg 107 relative to the torso.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practising the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A positioning system for positioning a patient for diagnostic imaging, the system comprising:
    a sensor arrangement comprising at least one sensor configured to provide a sensor signal indicative of at least one body parameter of the patient;
    a controller configured to determine a value of the at least one body parameter based on the sensor signal of the at least one sensor; and
    at least one actuatable support configured to move at least one of an arm and a leg of the patient with respect to a torso of the patient;
    wherein the controller is configured to actuate the at least one actuatable support depending on the determined value of the at least one body parameter to move at least one of the arm and the leg relative to the torso of the patient, such that the patient is guided to a posture for diagnostic imaging.

2. The positioning system according to claim 1,
    wherein the controller is configured to determine at least one of a morphology, a movement limitation, a mobility, and a flexibility of the patient based on the determined value of the at least one body parameter; and
    wherein the controller is configured to actuate the at least one actuable support depending on at least one of the determined morphology, the determined movement limitation, the determined mobility, and the determined flexibility of the patient.

3. The positioning system according to claim 2,
    wherein the controller is configured to move the actuatable support and/or to adjust the direction, speed, and/or magnitude of the movement of the actuatable support depending on at least one of the determined morphology, the determined movement limitation, the determined mobility, and the determined flexibility.

4. The positioning system according to claim 1, further comprising:
    at least one sensor for detecting a resistance and/or a force exerted by the patient against a movement of the at least one actuatable support; and/or
    at least one of a camera, a distance sensor, a laser distance sensor, an ultrasound sensor, a force sensor, a pressure sensor, and a contact sensor for detecting contact with at least one of a chin, a breast, a belly, an elbow, a hip, and a pelvis of the patient.

5. The positioning system according to claim 1,
    wherein the controller is configured to determine a movement limitation of at least one of the arm and the leg with respect to the torso of the patient based on the sensor signal of the at least one sensor; and/or
    wherein the controller is configured to actuate the at least one actuatable support depending on a movement limitation of at least one of the arm and the leg of the patient.

6. The positioning system according to claim 1,
wherein the at least one body parameter of the patient is at least one of a length of an extremity, a length of an arm, a length of a leg, a length of a neck, a belly size, a breast size, a spine shape, a movability of a body joint, a movability of a neck, a movability of a scapula, a movability of a shoulder, a movability of a knee, a movability of a hip, a movability of an ankle, a movability of a wrist, a movability of a chest, a movability of an elbow, a body height, and a corpulence.

7. The positioning system according to claim 1,
wherein the at least one actuatable support comprises at least one of a handle, an arm support, an armpit support, a footrest, a leg support, and an elastic band.

8. The positioning system according to claim 1,
wherein the at least one actuatable support is movable three-dimensionally and/or rotatable.

9. The positioning system according to claim 1,
wherein the at least one actuatable support comprises at least one handle for being grasped with at least one hand of the patient; and
wherein the controller is configured to move the at least one handle upward to stretch the patient and/or to move a scapula of the patient towards a spine of the patient.

10. The positioning system according to claim 1,
wherein the at least one actuatable support comprises a first handle for being grasped with a first hand of the patient and a second handle for being grasped with a second hand of the patient.

11. The positioning system according to claim 9,
wherein the controller is configured to move the first handle and the second handle upward and laterally outward in opposite directions to open the arms of the patient; and/or
wherein the controller (18) is configured to move the first handle and the second handle downward and towards a rear side of a detector of a diagnostic imaging apparatus, such that a distance between a scapula and a spine of the patient is increased.

12. The positioning system according to claim 1, further comprising:
a wall stand configured to encompass a detector and support the torso of the patient; and
at least one alignment element for aligning a vertical axis of the patient and a center axis of the detector based on moving the torso of the patient towards a center of the wall stand; and/or
b) a pivotable support for supporting a foot, a back, and/or a buttocks of the patient;
wherein the controller is configured to actuate the pivotable support such that the torso of the patient is moved towards a wall stand of the positioning system and/or towards a detector of a diagnostic imaging apparatus (100).

13. The positioning system according to claim 1, further comprising:
at least one instructing element for providing at least one of an acoustic, visual, audio-visual, and haptic instruction to the patient to guide the patient to the posture for diagnostic imaging.

14. An X-ray imaging apparatus, comprising:
an X-ray source;
an X-ray detector; and
a positioning system according to claim 1.

15. A method for operating a positioning system comprising a controller and a sensor to position a patient for diagnostic imaging, the method comprising:
processing, with a controller, a sensor signal of the sensor of the positioning system;
determining, with the controller (18), a value of at least one body parameter based on the sensor signal; and
actuating, with the controller, at least one actuatable support of the positioning system, the actuatable support being configured to move at least one of an arm and a leg of the patient with respect to a torso of the patient,
wherein the actuatable support is actuated in dependence of the determined value of the at least one body parameter, such that the patient is guided to a posture for diagnostic imaging based on moving at least one of the arm and the leg relative to the torso.

* * * * *